(12) United States Patent
Baltenneck et al.

(10) Patent No.: US 9,943,844 B2
(45) Date of Patent: Apr. 17, 2018

(54) MICROFLUIDIC EVALUATION SYSTEM FOR EVALUATING THE EFFICACY OF AN ANTIPERSPIRANT PRODUCT AND ASSOCIATED METHOD

(71) Applicant: L'OREAL, Paris (FR)

(72) Inventors: Fréderic Baltenneck, Chelles (FR); Jean-Baptiste Galey, Aulnay-sous-Bois (FR); Michel Dailly, Courtry (FR); Anne Colonna, Paris (FR); Fabrice Monti, Saulx les Chartreux (FR)

(73) Assignee: L'OREAL, Paris (FR)

( * ) Notice: Subject to any disclaimer, the term of this patent is extended or adjusted under 35 U.S.C. 154(b) by 203 days.

(21) Appl. No.: 14/784,693

(22) PCT Filed: Apr. 9, 2014

(86) PCT No.: PCT/EP2014/057114
§ 371 (c)(1),
(2) Date: Oct. 15, 2015

(87) PCT Pub. No.: WO2014/170174
PCT Pub. Date: Oct. 23, 2014

(65) Prior Publication Data
US 2016/0082433 A1 Mar. 24, 2016

(30) Foreign Application Priority Data
Apr. 15, 2013 (FR) ...................... 13 53403

(51) Int. Cl.
*G01N 33/15* (2006.01)
*G01N 33/48* (2006.01)
(Continued)

(52) U.S. Cl.
CPC ....... *B01L 3/5027* (2013.01); *B01L 3/502715* (2013.01); *G01N 33/15* (2013.01);
(Continued)

(58) Field of Classification Search
CPC ......... B01L 2200/10; B01L 2300/0654; B01L 2300/0663; B01L 2300/0867;
(Continued)

(56) References Cited

U.S. PATENT DOCUMENTS

| 6,632,619 B1 * | 10/2003 | Harrison | ............ B01J 19/0093 |
| | | | 422/504 |
| 2009/0014360 A1 * | 1/2009 | Toner | ................. B01D 21/0087 |
| | | | 209/208 |

(Continued)

FOREIGN PATENT DOCUMENTS

| FR | 2 934 778 A1 | 2/2010 |
| WO | WO-2005/089253 A2 | 9/2005 |

*Primary Examiner* — Jennifer Wecker
(74) *Attorney, Agent, or Firm* — Polsinelli PC (57) ABSTRACT

This applicator comprises a base (22) and a product applicator tongue (25) that projects from the base (22) along an axis (A-A'), said tongue (25) defining a central cavity (30). It comprises a massage element (32) disposed in the central cavity (30), with the massage (32) element and the tongue (25) defining therebetween in the cavity (30) an intermediary product retaining space (33). The massage element (32) and the tongue (25) can move in relation to one another transversally in relation to the axis (A-A').

23 Claims, 3 Drawing Sheets (51) Int. Cl.
  *G01N 33/50*   (2006.01)
  *A61Q 15/00*   (2006.01)
  *B01L 3/00*    (2006.01)
  *G01N 33/487*  (2006.01)
  *C12M 1/42*    (2006.01)

(52) U.S. Cl.
  CPC .... *G01N 33/4875* (2013.01); *B01L 3/502746* (2013.01); *B01L 2200/10* (2013.01); *B01L 2300/0654* (2013.01); *B01L 2300/0663* (2013.01); *B01L 2300/0867* (2013.01); *B01L 2300/16* (2013.01); *B01L 2400/0472* (2013.01); *B01L 2400/084* (2013.01)

(58) Field of Classification Search
  CPC ......... B01L 2300/16; B01L 2400/0472; B01L 2400/084; B01L 3/5027; B01L 3/052715; B01L 3/502746; G01N 33/15; G01N 33/4875
  See application file for complete search history.

(56)              References Cited

U.S. PATENT DOCUMENTS

| | | | |
|---|---|---|---|
| 2011/0045582 A1* | 2/2011 | Lee .................. | B01L 3/502707 |
| | | | 435/307.1 |
| 2011/0223222 A1* | 9/2011 | Spyros Botsaris ...... | A61K 8/34 |
| | | | 424/401 |
| 2013/0130243 A1* | 5/2013 | Livache ................ | B01L 3/5027 |
| | | | 435/6.11 |
| 2015/0253321 A1* | 9/2015 | Chou ............... | G01N 33/54366 |
| | | | 435/5 |

* cited by examiner

MICROFLUIDIC EVALUATION SYSTEM FOR EVALUATING THE EFFICACY OF AN ANTIPERSPIRANT PRODUCT AND ASSOCIATED METHOD

CROSS REFERENCE TO RELATED APPLICATIONS

This application is a National Phase filing under 35 U.S.C. § 371 of PCT/EP2014/057114 filed on Apr. 9, 2014; and this application claims priority to Application No. 1353403 filed in France on Apr. 15, 2013 under 35 U.S.C. § 119. The entire contents of each application are hereby incorporated by reference.

This invention relates to a microfluidic evaluation system for evaluating in vitro the efficacy of an antiperspirant product.

The antiperspirant products with an aluminum salt base (hydroxychloride of aluminum) have been known for nearly a century and are considered to be very effective in limiting the flow of axillary sweat after topical application.

It is however sought to substitute the current products with an aluminum salt base with products without aluminum salts or with a reduced amount of aluminum salts. In particular, the French Health Products Safety Agency recently published recommendations aimed at limiting to 2% the hydroxychloride of aluminum content of antiperspirant products, while the current content is between 10% and 30% in most of the products on the market.

Consequently, there is a need to develop antiperspirant products that differ from the current products with high aluminum salt content.

However, the development of antiperspirant products supposes that tests are available to evaluate the efficacy of the products developed.

To this effect, in order to evaluate the activity of the antiperspirant compounds such as antiperspirants with an aluminum salt base, it is possible to measure by gravimetry, in the framework of in vivo tests, the reduction in sweat formed on the surface of a zone treated with an antiperspirant product in the back or under the armpits of a subject in comparison with an untreated zone.

This method however does not provide full satisfaction. Indeed, it is long to implement, and therefore does not allow for a rapid evaluation of the antiperspirant potential of new products. In addition, it is difficult to implement for evaluating a substantial number of compounds, due to strict prerequisites.

Certain approaches, carried out in vitro, are based on the capacity that certain antiperspirant agents such as aluminum salts have in inducing the flocculation of proteins in an aqueous pH-neutral solution. This flocculation is in particular described in the articles entitled "The precipitation of mucine by aluminium" by C. Exley (Journal of Inorganic Biochemistry 70 (1998) 195-206) and "Interactions of Bovine Serum Albumin with Aluminum polyoxocations and aluminum hydroxide" by O. Deschaume and coil (Langmuir 22 (2006) 10078-10088). Other approaches, described in particular in the article entitled "Pharmacologic and Toxicologic effects of topically applied products on the eccrine sweat glands" by Rueller et al. (Advances in Modern toxicology, 1977, 4:1-59 Hemisphere Publishing Corp., Washington) are based on the clogging of certain filters in the presence of antiperspirant products.

These in vitro approaches do not provide full satisfaction. Indeed, their capacity in predicting the in vivo efficacy of new antiperspirant products is not satisfactory.

A purpose of the invention is to propose a device that makes it possible to test the efficacy of an antiperspirant product reliably and effectively and at least cost.

To this effect, the invention has for object an evaluation system such as defined hereinabove, comprising:
  a natural or artificial sweat source; and
  a microfluidic chip comprising a main flow channel for the antiperspirant product and at least one secondary flow channel for the sweat, the or each secondary channel comprising a sweat inlet that can receive sweat from the sweat source and a sweat outlet through which the secondary channel opens into the main channel, the or each secondary channel having a diameter of less than 100 µm.

According to particular embodiments, the evaluation system has one or several of the following characteristics, taken independently or in any technically permissible combination:
  the or at least one of the secondary channels is straight;
  the or at least one of the secondary channels comprises at least one section sinuous in shape;
  the system further comprises a measuring unit able to determine at least one physical-chemical parameter that represents the efficacy of the antiperspirant product flowing in the main channel;
  the measuring unit comprises at least a pressure sensor able to measure the pressure in the or each secondary channel;
  the measuring unit comprises an imaging tool able to form an image of the zone of confluence between the sweat coming from the or from each secondary channel and the antiperspirant product flowing in the main channel;
  the system further comprises:
    a first injection device connected to the sweat source and configured to inject the sweat from the sweat source into the or each secondary channel at a determined injection flow rate;
    a second injection device configured to inject the antiperspirant product into the main channel at a determined injection flow rate,
  the main channel is open over its entire length over a portion of its circumference;
  the microfluidic chip comprises at least:
    one set of secondary channels comprising at least two secondary channels, and
    at least one channel for distributing sweat comprising a sweat distribution inlet intended to be connected to the sweat source and sweat distribution outlets through which the distribution channel opens into the secondary channels of the set in such a way that the secondary channels of the set of secondary channels are supplied with sweat in parallel by the channel for distributing sweat;
  the walls of the or of each secondary channel are functionalized by proteins;
  the main channel has a cross-section that is strictly greater than the cross-section of the or of each secondary channel;
  the microfluidic chip comprises at least two secondary channels opening into the main channel;
  the or each main channel has a cross-section of diameter between approximately 100 µm and approximately 1000 µm, and preferably approximately equal to 500 µm;
  the or each secondary channel has a cross-section of diameter between 10 µm and 100 µm and preferably between environ 30 µm and 60 µm;

the microfluidic chip further comprises at least two inlet channels each intended to receive an antiperspirant product or a component of an antiperspirant product, the inlet channels opening into the main channel upstream of the or of each sweat outlet of the or of each secondary channel.

The invention also has for object a method for evaluating the efficacy of an antiperspirant product, comprising the steps of:
- supplying a microfluidic evaluation system such as described hereinabove;
- injecting sweat into the or each secondary channel of the microfluidic chip from the sweat source;
- injecting antiperspirant product into the main channel;
- determining at least one physical-chemical parameter that represents the efficacy of the antiperspirant product; and
- evaluating the efficacy of the antiperspirant product using the or each physical-chemical parameter measured.

According to particular embodiments, the evaluation method according to the invention has one or several of the following characteristics, taken independently or in any technically permissible combination:
- the sweat is injected into the or each secondary channel in pulse mode or in continuous mode;
- the step of injecting sweat comprises:
  - injecting sweat into the or each secondary channel at a filling flow rate until the or each secondary channel is filled with sweat, then
  - injecting sweat into the or each secondary channel at a distribution flow rate strictly less than the filling flow rate;
- the step of injecting sweat comprises:
  - injecting sweat into the or each secondary channel at a distribution flow rate; then
  - injecting sweat into the or each secondary channel at an unclogging flow rate that is strictly greater than the distribution flow rate, and advantageously increasing progressively over time;
- the physical-chemical parameter that represents the efficacy of the antiperspirant product determined in the step of determining is a parameter that represents the existence of a clog in the or each secondary channel 9; and
- it is concluded that the antiperspirant product is effective if the existence of a clog was determined in the step of determining.

The invention also has for object a method for manufacturing an evaluation system such as described hereinabove, comprising a step of manufacturing the microfluidic chip, said step comprising:
- manufacturing a block comprising the or each secondary channel and the main channel;
- treating this block in such a way as to render the walls of the or of each secondary channel able to form connections with the proteins intended to be grafted on the walls of the or of each secondary channel; and
- injecting into the or each secondary channel a solution containing the proteins intended to be grafted in the secondary channels in such a way that the proteins form connections with the walls of the secondary channels.

According to particular characteristics:
- the treatment of the block in order to render the walls hydrophilic is a treatment via an oxygen plasma torch;
- the block comprising the or each secondary channel and the main channel is manufactured via molding using a mold with a suitable shape;
- the block is made from a material able to be molded in liquid state, in particular from PDMS.

The invention also has for object a microfluidic chip comprising:
- a main flow channel suited for the flow of antiperspirant product; and
- at least one secondary channel suited for the flow of sweat, the or each secondary channel comprising a sweat inlet that can receive sweat coming from a natural or artificial sweat source and a sweat outlet through which the secondary channel opens into the main channel, the or each secondary channel having a diameter of less than 100 µm.

According to particular embodiments, the microfluidic chip has one or several of the following characteristics, taken independently or in any technically permissible combination:
- the or at least one of the secondary channels is straight;
- the or at least one of the secondary channels comprises at least one section sinuous in shape;
- the main channel is open over its entire length over a portion of its circumference;
- the microfluidic chip comprises at least:
  - one set of secondary channels comprising at least two secondary channels, and
  - at least one channel for distributing sweat comprising a sweat distribution inlet intended to be connected to the sweat source and sweat distribution outlets through which the distribution channel opens into the secondary channels of the set in such a way that the secondary channels of the set of secondary channels are supplied with sweat in parallel by the channel for distributing sweat;
- the walls of the or of each secondary channel are functionalized by proteins;
- the main channel has a cross-section that is strictly greater than the cross-section of the or of each secondary channel;
- each set of secondary channels substantially has a comb shape, the secondary channels forming the teeth of the comb, all of the sets of secondary channels, opening into the same main channel.

The invention will be easier to understand in view of the following description, provided solely as an example and with reference to the appended drawings, wherein.

In the following description, the terms upstream and downstream are used in reference to the direction of flow of the liquids.

Moreover, the term "diameter" means the maximum transversal extent of the channel considered, for example the diameter of a circle in the case where the transversal section of the channel is circular or the diagonal of a rectangle in the case where the transversal section is rectangular.

Figure 1:
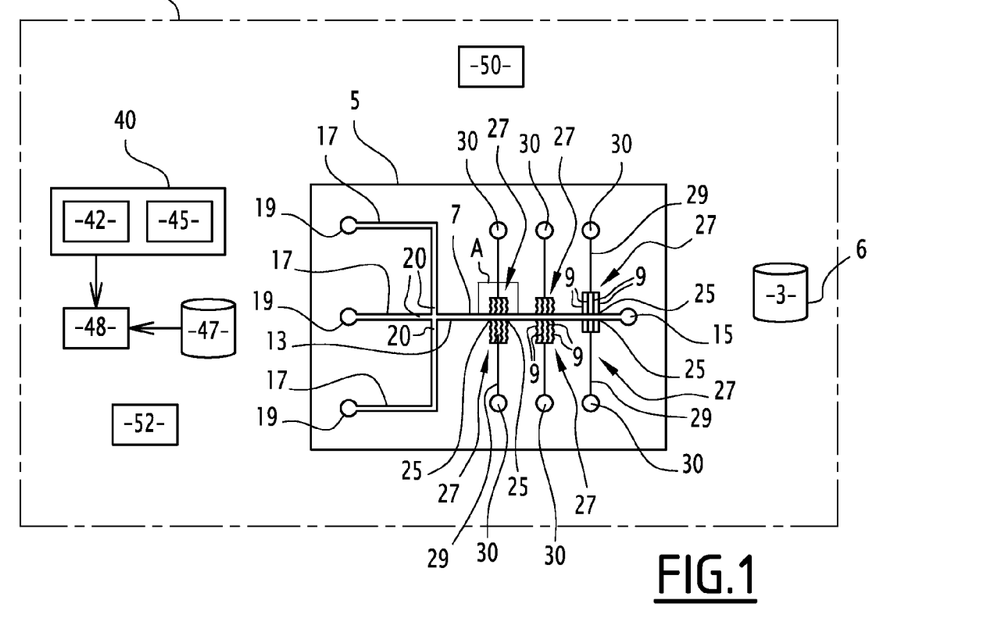
FIG. 1 is a diagrammatical top view of an evaluation system according to a first embodiment of the invention.

FIG. 1 shows an example of a microfluidic evaluation system 1 according to a first embodiment of the invention.

The evaluation system 1 is provided for evaluating in vitro the efficacy of an antiperspirant product. It comprises a natural or artificial source of sweat 3 and a microfluidic chip 5.

The sweat source 3 comprises for example a container 6 containing natural sweat or artificial sweat. The container 6 can also contain a mixture of natural and artificial sweat.

The natural sweat is the biological liquid secreted by the sweat glands during the phenomenon of transpiration. The natural sweat of the sweat source 3 was for example sampled beforehand from a human being using any method known to those skilled in the art.

The artificial sweat is for example a BSA artificial sweat comprising:
sodium chloride (NaCl)
lactic acid
urea
BSA
ammonia in sufficient quantities to obtain a substantially neutral pH, the rest being constituted of water.

"BSA" is the abbreviation used by those skilled in the art to designate "bovine serum albumin". The bovine serum albumin sold under the designation Sigma A-4503 by Sigma-Aldrich is used for example.

Alternatively, any other type of artificial sweat known to those skilled in the art can be used in the scope of the invention.

The microfluidic chip 5 comprises at least one main flow channel 7 of the antiperspirant product and at least one secondary flow channel 9 of the sweat.

The main channel 7 is intended to receive a flow of antiperspirant product to be tested.

The secondary channels 9 open into the main channel 7. They are intended to receive a flow of natural or artificial sweat from the sweat source 3.

The main channel 7 models the surface of the skin, while the secondary channels 9 model the sweat channels opening onto the surface of the skin.

The main channel 7 comprises an antiperspirant product inlet 13 through which the antiperspirant product enters into the main channel 7, and an antiperspirant product outlet 15 through which the antiperspirant product is evacuated outside of the microfluidic chip 5. The antiperspirant product inlet 13 and the antiperspirant product outlet 15 are spaced apart according to the direction of flow of the antiperspirant product in the main channel 7.

The antiperspirant product outlet 15 is intended to be connected to an outlet hose 16, in particular made of plastic material, and for example of PEEK (poly-ether-ether-ketone). This outlet hose can be seen in FIG. 3. It is used to evacuate the antiperspirant product, possibly mixed with sweat, outside of the microfluidic chip 4.

The main channel 7 is substantially straight between its antiperspirant product inlet 13 and its antiperspirant product outlet 15.

In the embodiment shown, the main channel 7 is delimited by a substantially cylindrical wall, for example with a circular or rectangular section. As such, it is closed over its entire circumference over its entire length, except for the orifices through which the secondary channels 9 open into the main channel 7.

A main channel 7 with a rectangular section is preferred. Indeed, such a channel is easier to manufacture.

The main channel 7 advantageously has a cross-section of diameter greater than approximately 100 µm. It has for example a cross-section of diameter between approximately 100 µm and approximately 1000 µm. Advantageously, the diameter of the cross-section of the main channel 7 is approximately equal to 500 µm.

Cross-section means the section perpendicular to the axis of the main channel 7.

In the evaluation system 1 according to the first embodiment shown in FIG. 1, the microfluidic chip 5 comprises exactly one main channel 7.

In this embodiment, the microfluidic chip 5 further comprises at least two inlet channels 17. Each inlet channel 17 is intended to receive an antiperspirant product or a component of an antiperspirant product. Each inlet channel 17 extends upstream of the main channel 7 being in fluidic communication with the main channel 7.

More particularly, each inlet channel 17 comprises an inlet 19 opening outside of the microfluidic chip 5. It comprises an outlet 20 opening into the main channel 7 on the inlet 13 of the main channel 7.

The inlets 19 of the inlet channels 17 are able to be connected to devices for injecting antiperspirant product.

In the example shown, the microfluidic chip 5 comprises three inlet channels 17 each opening into the main channel 7.

The microfluidic chip 5 comprises, in the example shown, a plurality of secondary channels 9 each opening into the main channel 7 downstream of the antiperspirant product inlet 13 of the main channel 7. In particular, it comprises at least two secondary channels 9 each opening into the main channel 7 downstream of the antiperspirant product inlet 13 of the main channel 7.

Each secondary channel 9 comprises a sweat inlet 23 through which the sweat from the sweat source 3 enters in the secondary channel 9 and a sweat outlet 25, through which the sweat exits from the secondary channel 9. The secondary channel 9 opens into the main channel 7 via the sweat outlet 25.

Each secondary channel 9 has a cross-section of diameter less than or equal to 100 µm. Preferably, each secondary channel 9 has a cross-section of diameter between approximately 10 µm and approximately 100 µm. Advantageously, the diameter of the cross-section each secondary channel 9 is between 30 µm and 60 µm. These diameters are chosen in such a way that they reproduce those of the eccrine sweat glands (acrosyringium) native to man. Cross-section means the section perpendicular to the axis of the secondary channel 9.

Preferably, the diameter of the cross-section of the main channel 7 is strictly greater than the diameter of the cross-section of the secondary channels 9.

In the embodiment shown in FIG. 1, the microfluidic chip 5 comprises secondary channels 9 sinuous in shape. These secondary channels 9 sinuous in shape can in particular be seen in FIG. 2. This sinuous shape models the spring winding of the upper portion of the eccrine sweat channels native to man.

It further comprises secondary channels 9 of straight shape. Such secondary channels 9 of straight shape are in particular shown on the right in FIG. 1. The secondary channels 9 of straight shape are delimited by cylindrical walls, for example with a rectangular or circular base.

The secondary channels 9 of straight shape have the advantage of being easier to manufacture than the secondary channels 9 sinuous in shape.

In the example shown, the secondary channels 9 extend along an axis that is substantially perpendicular to the axis of the main channel 7. They open at a right angle into the main channel 7. This particular direction of extension of the secondary channels 9 has the advantage of facilitating the microfabrication of the microfluidic chip 5.

Alternatively, the axes of the secondary channels 9 extend along any other direction that can be considered by those skilled in the art.

More particularly, in the microfluidic chip 5 according to the first embodiment, the microfluidic chip 5 comprises sets 27 of secondary channels 9. Each set 27 comprises at least two secondary channels 9 supplied with sweat by a common channel for distributing sweat 29. As such, the secondary channels 9 of the same set 27 are supplied with sweat in parallel from the distribution channel 29.

The distribution channel 29 comprises a sweat distribution inlet 30 that opens outside of the microfluidic chip 5. The sweat distribution inlet 30 is able to be connected to the sweat source 3 by the intermediary of a sweat injection device outside of the microfluidic chip 5.

The distribution channel 29 further comprises sweat distribution outlets 32, located downstream of the sweat distribution inlet 30, through which it opens into the secondary channels 9 of the set 27 of secondary channels 9. More particularly, each sweat distribution outlet 32 opens into a respective secondary channel 9 of the set 27.

More particularly, the distribution channel 29 comprises for example a first section 31 followed, in the direction of flow of the sweat, by a second section 33 extending substantially perpendicularly to the first section 31 and opening into the secondary channels 9 of the set 27 of secondary channels 9 in such a way as to distribute the sweat coming from the first section 31 in these secondary channels 9.

In the example shown, the first section 31 and the second section 33 of the distribution channel 29 are substantially straight.

The first section 31 extends along an axis that is substantially parallel to the axis of the secondary channels 9 of the set 27 of secondary channels 9. The second section 33 extends along an axis that is substantially parallel to the axis of the secondary channels 9 into which they open.

For example the first section 31 is delimited by a substantially cylindrical wall, for example with a circular or preferentially rectangular base. It comprises the sweat distribution inlet 30 at its upstream end, taken along the axis of the first section 31. The second section 33 is delimited by a substantially cylindrical wall, for example with a circular or preferentially rectangular base. The sweat distribution outlets 32 are formed by orifices made in this wall and spaced apart along the direction of the axis of the second section 33.

Each set 27 of secondary channels 9 substantially has a comb shape, the secondary channels 9 forming the teeth of the comb.

Figure 2:
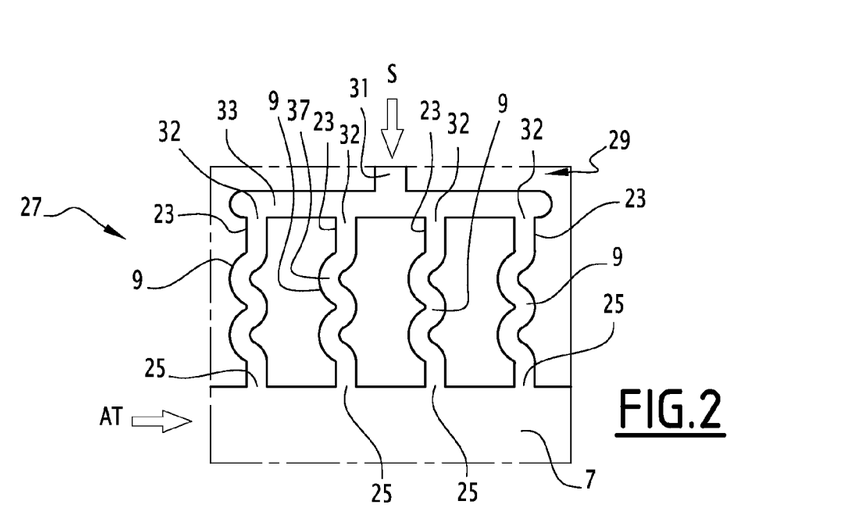
FIG. 2 is a diagrammatical top view of the detail noted as A of the evaluation system of FIG. 1.

In the example shown in FIGS. 1 and 2, all of the sets 27 of the secondary channels 9 open into the same main channel 7.

Advantageously, all of the secondary channels 9 of the same set 27 of secondary channels 9 have the same shape, sinuous or straight and/or the same dimensions, in particular the same diameter.

In the embodiment shown in FIG. 1, the microfluidic chip 5 comprises both sets 27 comprising only secondary channels 9 sinuous in shape and sets 27 comprising only secondary channels of straight shape.

FIG. 2 shows more particularly a set 27 comprising only secondary channels 9 sinuous in shape.

In the embodiment shown in FIG. 1, the microfluidic chip 5 comprises at least one first set 27 and a second set 27 comprising only secondary channels 9 of the same shape, for example sinuous or straight, but with diameters of the secondary channels 9 of the first set 27 and of the second set 27 that are different.

The microfluidic chip 5 comprises for example the following sets 27 of secondary channels:
a set 27 comprising only secondary channels 9 sinuous in shape that have a first diameter, for example equal to approximately 30 μm,
a set 27 comprising only secondary channels 9 sinuous in shape that have a second diameter, different from the first diameter, for example equal to approximately 60 μm,
a set 27 comprising only secondary channels 9 of straight shape that have a third diameter, for example equal to the first diameter, and in particular equal to approximately 30 μm; and
a set 27 comprising only secondary channels 9 of straight shape that have a fourth diameter, for example equal to approximately the second diameter, and in particular equal to approximately 60 μm.

According to another embodiment, all of the sets 27 of secondary channels 9 of the microfluidic chip 5 comprise the same number of secondary channels 9. They comprise for example four secondary channels 9. Alternatively, they comprise for example two secondary channels 9 or any other suitable number of secondary channels 9.

Alternatively, at least two of the sets 27 of secondary channels 9 have numbers of secondary channels 9 that are different, for example two secondary channels 9 for one and four secondary channels 9 for the other.

Advantageously, the secondary channels 9 of some of the sets 27 of secondary channels 9 of the microfluidic chip 5 open into the main channel 7 via a first side of the main channel 7, taken perpendicularly to the axis of the main channel 7, while the secondary channels 9 of the other sets 27 open into the main channel 7 by a second side of the main channel 7 opposite the first side perpendicularly to the axis of the main channel 7.

In the example shown, each set 27 of secondary channels 9 extends facing another set 27 of secondary channels 9 arranged on the opposite side of the main channel 7 perpendicularly to the axis of the main channel 7. As such, the microfluidic chip 5 comprises pairs of sets 27 facing each other on either side of the main channel 7.

Advantageously, the two sets 27 of a pair of sets 27 have secondary channels 9 of the same shape, straight or sinuous, but of a different diameter.

For example, all of the sets 27 arranged on the same side of the main channel 7 have secondary channels that have substantially identical diameters.

The evaluation system 1 further comprises a first injection device 50, configured to inject the sweat into the secondary channels 9 from the sweat source 3 at a controlled injection flow rate.

The evaluation system 1 further comprises a second injection device 52, configured to inject the antiperspirant product into the main channel 7 at a controlled injection flow rate.

The first injection device 50 and the second injection device 52 comprise for example a syringe pump or an electronic pump, connected to the corresponding inlets of the microfluidic chip 5 by connection tubes. The connection tubes are preferably made from a material that is inert with regards to the components of sweat, in particular made of PEEK (poly-ether-ether-ketone).

Figure 3:
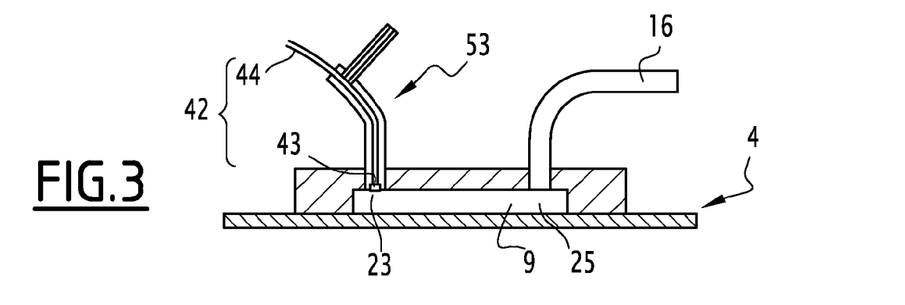
FIG. 3 is a diagrammatical cross-section view of the location of a pressure sensor in the secondary channel of the microfluidic chip of an evaluation system according to the invention.

Such a connection tube 53 connected to the inlet of a secondary channel 9 and used to inject the sweat into this secondary channel 9 is shown in FIG. 3.

More particularly, in the evaluation system 1 according to the first embodiment, the first injection device 50 is connected to the sweat distribution inlets 30. The second injection device 52 is connected to the inlets 19 of the inlet channels 17.

The evaluation system 1 further comprises a measuring unit 40, able to measure at least one physical-chemical parameter that represents the efficacy of the antiperspirant product.

It is generally admitted that the antiperspirant effect of certain antiperspirant products, in particular comprising aluminum chlorohydrate (ACH), results from the formation of a clog at the outlet of the sweat pore which results in a reduction in the flow of outgoing sweat. The formation of this clog results from the reaction of the sweat with the antiperspirant product, and more particularly of the distribution in the sweat pore of the aluminum salt contained in the antiperspirant product, followed by a flocculation of the proteins and glycoproteins of the sweat and of the wall of the sweat channel according to the mechanism described in the articles entitled "Mechanism of antiperspirant action of aluminum salts" by Holzle and Kligman (J. Soc. Cosm. Chem. 30(1979) 279-295) as well as "The mechanism of antiperspirant action of aluminum salts" by Quatrale and coil (J. Soc. Cosm. Chem. 31(1981) 107-136) and "Pharmacologic and Toxicologic effects of topically applied products on the eccrine sweat glands" by Rueller et al. (Advances in Modern toxicology, 1977, 4:1-59 Hemisphere Publishing Corp., Washington).

In the microfluidic chip 5 according to the invention, the outlet of the sweat pores is modeled by the outlets 25 of the secondary channels 9.

In light of the preceding, the physical-chemical parameter that represents the efficacy of the antiperspirant product is for example a parameter that represents the existence of a clog at the outlet of the secondary channel 9, i.e. in the zone of confluence between the antiperspirant product flowing in the main channel 7 and the sweat flowing in the secondary channel 9 considered, or a parameter that represents the solidity of this clog.

The measuring unit 40 is for example able to measure one or several physical-chemical parameters chosen from the list consisting of: the side of the clog, the subsistence duration of the clog before unclogging of the secondary channel 9, the speed of the formation of the clog, the resistance before unclogging of the secondary channel 9 measured for example by the total volume of sweat injected until unclogging and the pressure reached in the secondary channel 9 before unclogging.

The measuring unit 40 comprises for example at least one pressure sensor 42 configured to measure, advantageously continuously, the pressure in the secondary channels 9. Advantageously, the measuring unit 40 comprises a pressure sensor 42 in each secondary channel 9.

For reasons of simplifying the drawings, the pressure sensor 42 is shown only diagrammatically in FIGS. 1 and 2.

FIG. 3 shows an example arrangement of the pressure sensor 42 in a secondary channel 9 of the microfluidic chip 5. The pressure sensor 42 comprises a pressure sensor 43 arranged on the sweat inlet 23 of the secondary channel 9 in such a way as to measure the pressure in this secondary channel 9.

In the example shown, the connection tube 53 connected to the sweat inlet of the secondary channel 9 is in the form of a T junction, and the pressure sensor 42 is inserted into this connection tube 53.

More particularly, the pressure sensor 43 comprises a membrane of which the displacement represents the pressure in the secondary channel 9. The pressure sensor 42 further comprises an optical fiber 44 connected to the pressure sensor 43 and extending through the connection tube 53 in such a way as to transmit the displacement of the membrane of the pressure sensor 43 to an analyzer located outside the microfluidic chip 5 and able to determine the pressure in the secondary channel 9 according to the displacement measured.

In this example, the connection tube 53 comprises a branch connected to the sweat injection device 50 and a branch through which the optical fiber 44 is introduced into the connection tube 53.

Alternatively, any other pressure sensor 42 able to allow for the measuring of the pressure in the secondary channel 9 can be used.

In the case where the measuring unit 40 comprises a pressure sensor 42, the physical-chemical parameter measured by the measuring unit 40 comprises the pressure in the secondary channel 9 considered Measuring the pressure makes it possible to assess the efficacy of the clog of the secondary channel 9 under the action of the antiperspirant product flowing in the main channel 7. In particular, it makes it possible to detect the formation of a clog at the outlet of the secondary channel 9 considered, the disappearance of this clog, the subsistence duration of the clog, the speed of the formation of the clog, the pressure reached in the secondary channel 9 before unclogging. In particular, the formation of a clog coincides with a rapid increase in the pressure in the secondary channel 9. The disappearance of the clog coincides with a sudden decrease in the pressure in the secondary channel 9. The subsistence duration of the clog corresponds to the interval of time between the formation and the disappearance of the clog. The speed of the formation of the clog corresponds to the interval of time between the beginning of the experience and the formation of the clog. The pressure reached in the secondary channel 9 before unclogging corresponds to the maximum pressure measured.

Alternatively or as an option, the measuring unit 40 comprises an imaging tool 45 able to form an image of at least the zone of confluence between the sweat coming from a secondary channel 9 considered and the antiperspirant product flowing in the main channel 7, i.e. in particular at least the outlet 25 of this secondary channel 9.

Advantageously, the imaging tool 45 is able to form an image of the microfluidic chip 5.

The imaging tool 45 comprises for example a microscope, combined advantageously with a camera able to record the images viewed in the microscope.

Figure 4:
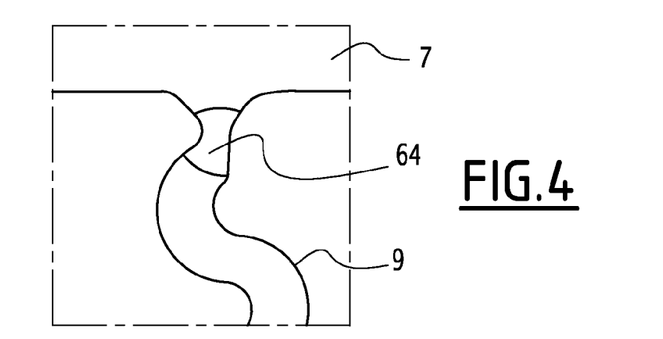
FIG. 4 is a diagrammatical top view of a portion of the evaluation system 1 of FIG. 1 showing a clog formed in a secondary channel of the microfluidic chip.
Figure 5:
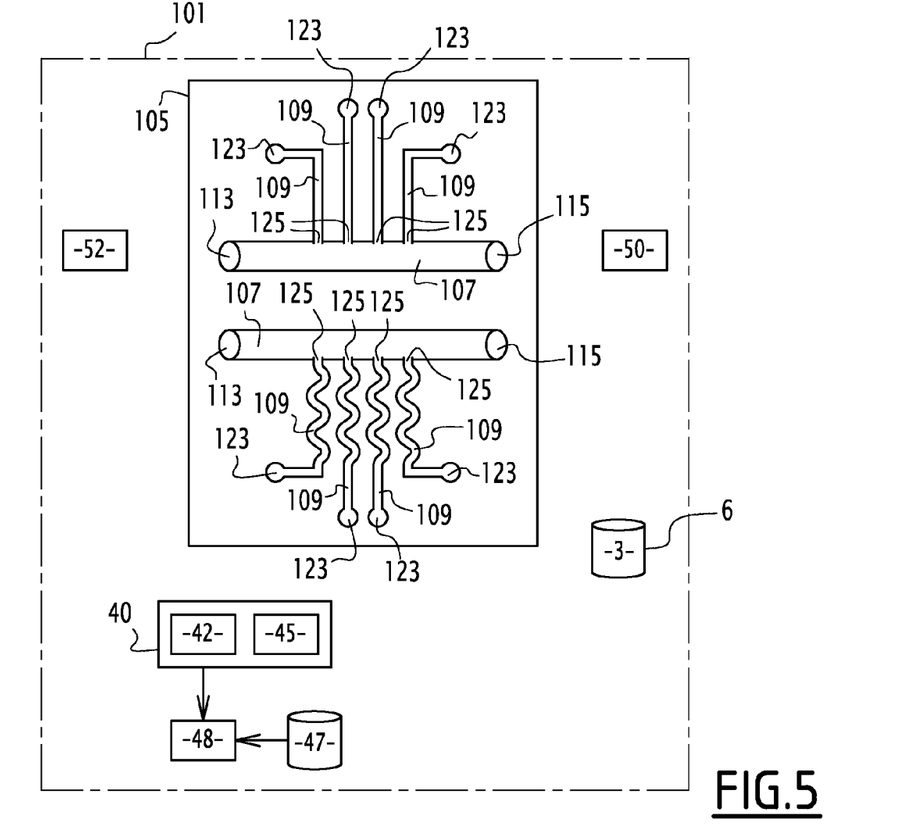
FIG. 5 is a diagrammatical top view of an evaluation system according to a second embodiment.

Advantageously, the imaging tool 45 is able to create images in optical microscopy in phase contrast. Such an image is shown in FIG. 5. The images in phase contrast microscopy obtained as such make it possible to detect flocs, aggregates and clogs blocking the flow of sweat as shown in FIG. 4.

Alternatively or as an option, the imaging tool is able to create fluorescence microscopy images. In this case, the sweat flowing in the secondary channels 9 contains a fluorescent coloring, for example fluorescein. The images obtained with fluorescence microscopy make it possible to better visualize the formation of clogs and the blocking of the sweat.

Alternatively, the imaging tool 45 comprises any other device known to those skilled in the art that makes it possible to create images via microscopy and/or spectroscopy, as well as, preferably, the recording thereof.

When the measuring unit 40 comprises an imaging tool 45, the physical-chemical parameter that represents the efficacy of the antiperspirant product is for example determined visually from images obtained by the imaging tool 45. In particular, the observation of images obtained by the imaging tool 45 makes it possible to visually detect the formation and the disappearance of a clog, the size of the clog, the speed of formation of the clog, as well as its subsistence duration.

Optionally, the measuring unit 40 comprises image processing software, configured to automatically determine at least some of the physical-chemical parameters listed hereinabove by image processing obtained by the imaging tool 45.

The efficacy of the antiperspirant product is deduced by comparing at least one of the physical-chemical parameters determined by the measuring unit 40 with a predetermined threshold value of this parameter, which may be Boolean.

The predetermined threshold values of each physical-chemical parameter are for example stored in a database 47.

According to an embodiment, the evaluation system 1 comprises an interpretation unit 48 configured to carry out this comparison automatically and conclude as to the efficacy of the antiperspirant product tested from determined physical-chemical parameters and corresponding threshold values.

Alternatively, this comparison is carried out manually by an operator.

The evaluation system 1 according to the invention is particularly advantageous, in particular thanks to the properties of the microfluidic chip 5.

Indeed, it makes it possible to obtain in vitro results that are particularly reliable, and in particular for which the reliability is close to that of in vivo tests. This reliability is the result of the fact that the microfluidic chip 5 accurately reproduces the confinement that exists on a sweat channel by the dimensions of its secondary channels 9, and the distribution capacity of the antiperspirant product in the sweat by its network of secondary channels 9 and principal 7.

It is furthermore relatively inexpensive to use, and in particular less expensive than in vivo tests.

Moreover, since the tests are not carried out in vivo, the evaluation system according to the invention simplifies the test process considerably. On the other hand, it makes it possible to rapidly evaluate a large number of antiperspirant products.

The invention also has for object a method for manufacturing the evaluation system 1.

The manufacturing process comprises a step of manufacturing the microfluidic chip 5 of the evaluation system 1 comprising the steps of:

pouring a mixture of liquid PDMS (polydimethylsiloxane) and cross-linking agent in a mold of adapted shape, in particular made from silicon, baking this mixture in an oven in such a way as to obtain a block comprising the main channel 7 and the secondary channel or channels 9;

piercing in this block the inlets and outlets of the microfluidic chip 4, in particular using a punch of a size equal to that of the connection tubes of the microfluidic chip 5 in injection devices 50, 52 of fluids (sweat and antiperspirant agent) intended to be connected to these inlets;

gluing the block transformed as such on a support, advantageously transparent, constituted in particular by a glass plate.

The support advantageously forms the bottom of the main channel 7 and of the secondary channel or channels 9.

The block obtained at the end of the step of baking has for example a thickness between 3 mm and 10 mm, and for example equal to approximately 5 mm.

During the step of baking, the PDMS/anti-cross-linking agent mixture contained in the mold is for example baked at 90° C. for a duration equal to at least 24 hours in order to harden it.

Advantageously, the method of manufacture comprises, before the step of pouring, a step of manufacturing the mold in a block of silicon by any etching process known to those skilled in the art, in particular by photolithography. This mold will make it possible to manufacture a series of microfluidic chips 4.

According to a first alternative, the walls of the secondary channels 9 are functionalized with proteins. These proteins are connected to the walls of the secondary channels 9 by chemical bonds. These chemical bonds are for example covalent bonds, hydrogen bonds or ionic bonds. Preferably, these are hydrogen bonds.

The proteins chosen are proteins that are able to reproduce the environment that exists in a sweat channel. The protein used is for example a mucine, which is a glycoprotein known for lining the epithelium of the acrosyringium, or a keratin, which is the main constituent of the corneocytes of the surface of the sweat pore. Such secondary channels 9 are advantageous, as they mime even better the interactions that occur in the sweat channel.

The process for manufacturing the microfluidic chip 5 according to this alternative differs from the method described hereinabove only in that, after the manufacture of the block containing the channels 7, 9, this block is treated in such a way that the secondary channels 9 are able to form connections with the proteins.

Preferably, the block is treated by means of an oxygen plasma torch in such a way as to render hydrophilic the walls of the secondary channels. The proteins are then bonded to the walls of the secondary channels 9 by hydrogen bonds.

Then, in particular after the gluing of the block on the support, a solution containing the proteins is injected into the secondary channels 9 in such a way that the proteins bond to the walls of the secondary channels 9.

According to a second alternative (not shown), the wall of the main channel 7 is not cylindrical. The main channel 7 is not closed over its entire length over its entire circumference.

According to this alternative, the main channel 7 is open over its entire length over at least one portion of its circumference. It has an open contour cross-section. The main channel 7 as such has the shape of a gutter.

In particular, the main channel 7 has a rectangular cross-section. It comprises a bottom wall formed in particular by the support, and in particular by the glass plate, and side walls extending upwards from the bottom wall. It does not comprise an upper wall, and is open on the side opposite the bottom wall.

Such an open main channel 7 models more exactly the actual configuration on the surface of the skin onto which the sweat channels open. Indeed, the antiperspirant product flowing in the main channel 7 can then dry in the air.

The invention also has for object a method for evaluating the efficacy of an antiperspirant product comprising the following steps:
- supplying an evaluation system 1 such as described hereinabove;
- injecting natural and/or artificial sweat into the or each secondary channel 9 of the microfluidic chip 5 from the sweat source 3;
- injecting at least one antiperspirant product into the main channel 7;
- determining at least one physical-chemical parameter that represents the efficacy of the antiperspirant agent considered; and
- evaluating the efficacy of the antiperspirant product using the determined physical-chemical parameter.

During the step of supplying the evaluation system 1, the microfluidic chip 5 is provided such as defined hereinabove. The first injection device 50 is connected as an inlet to the sweat source 3. It is connected at the outlet to the distribution inlets 30 of the distribution channels 29 in such a way as to inject the sweat at a controlled flow rate into the secondary channels 9 via the distribution channels 29.

The second injection device 52 is connected to the inlets 19 of the inlet channels 17 in such a way as to inject the antiperspirant product at a controlled flow rate into the main channel 7 via the inlet channels 17.

During the step of injecting sweat, the sweat is injected into the secondary channels 9 by means of the first injection device 50.

Advantageously, during this step, the sweat is injected at a first injection flow rate between 0.01 nL and 100 nL/s, preferably equal to 0.1 nL/s.

The sweat is injected in constant mode or in pulse mode.

Constant mode means that the sweat is continuously injected into the secondary channels 9.

Pulse mode means in particular that the sweat is injected in successive stages of injection flow rates, in particular according to a predetermined temporal sequence. As such, for example, the sweat is injected for 5 min at an injection flow rate equal to 1 nL/s then the injection flow rate is set to zero for 5 min, then injection again at an injection flow rate of 1 nL/s for 5 min, and so on by repeating the cycle described hereinabove as often as necessary.

As shall be described in more detail in what follows, the sweat injection flow rate is advantageously variable over time.

During the step of injection of the antiperspirant product, the antiperspirant product is injected into the main channel 7 by leans of the second injection device 52. Advantageously, during this step, the antiperspirant product is injected at a second injection flow rate between 0.01 nL and 100 nL/s, preferably equal to 1 nL/s.

The injection flow rate of the antiperspirant product is advantageously variable over time.

The steps of injecting sweat and of injecting antiperspirant product are simultaneously or overlap at least partially.

Advantageously, the injecting of sweat continues after the stopping of the injecting of the antiperspirant product, in particular in order to allow for the unclogging of the secondary channels 9, which may be clogged due to the reaction of the antiperspirant product with the sweat.

Advantageously, the steps of injecting comprise a step of filling of the or of each secondary channel 9 and of the main channel 7 in such a way as to fill the or each secondary channel 9 with sweat and to fill the main channel 7 with antiperspirant agent.

In particular, during the step of filling, the filling flow rate of the secondary channels 9 is between 0.1 and 0.5 nL/s and more particularly approximately equal to 0.2 nL/s.

The filling flow rate of the main channel 7 is between 0.1 and 10 nL/s, and more particularly equal to 1 nL/s.

The step of filling is followed by a step of distributing, during which the antiperspirant product flowing in the main channel 7 and the sweat flowing in the secondary channel or channels 9 react together, in particular on the zones of confluence between the sweat flowing in the secondary channel or channels 9 and the antiperspirant product flowing in the main channel 7. According to the efficacy of the antiperspirant product, during this step of distributing, the interaction between the sweat and the antiperspirant product leads to the formation of clogs at the outlet 25 of the secondary channel or channels 9.

During this step of distributing, the sweat is injected into the secondary channel or channels 9 at a sweat distribution flow rate, and the antiperspirant agent is injected into the main channel 7 at a distribution flow rate of the antiperspirant agent.

The sweat distribution flow rate is, preferably, strictly less than the filling flow rate of the secondary channel or channels 9. It is for example less than half of the filling flow rate of the secondary channels 9.

A sweat distribution flow rate less than the filling flow rate of the secondary channels 9 is advantageous because it allows for finer control during the evaluation test of the efficacy of the antiperspirant agent or a faster filling of the secondary channels 9.

Alternatively, the sweat distribution flow rate is equal to the filling flow rate of the secondary channels 9.

The antiperspirant agent distribution flow rate is for example equal to the filling flow rate of the main channel 7.

Further advantageously, the step of distributing is followed by a step of unclogging the secondary channel or channels 9 during which the sweat is injected at an unclogging flow rate, advantageously higher than the sweat distribution flow rate.

Preferably, during the step of unclogging, the injection flow rate of sweat into the secondary channels 9 is progressively increased. This step of unclogging makes it possible to accelerate the expulsion of the clog that may be formed at the outlet 25 of the secondary channel 9 considered.

For example, during this step, the sweat flow rate is progressively increased by a factor between 20 and 30 between the beginning of the step of unclogging and the end of the step of unclogging.

Preferably, the injection of the antiperspirant product is stopped during the unclogging phase.

The table below shows an example of the method for evaluating the efficacy of an antiperspirant product.

TABLE 1

| Step | Filling | Distribution | Unclogging | | | |
|---|---|---|---|---|---|---|
| Duration | Until filling of the channel 7, 9 concerned | 15 min | 15 min | 4 min | 2 min | Until the unclogging of the channels 9 |
| | | | Injection flow rates | | | |
| Secondary channels 9 | 0.2 nL/s | 0.1 nL/s | 0.3 nL/s | 1 nL/s | 2 nL/s | 3 nL/s |
| Main channel 7 | 1 nL/s | 1 nL/s | 0 nL/s | 0 nL/s | 0 nL/s | 0 nL/s |

The step of determining at least one physical-chemical parameter that represents the efficacy of the antiperspirant agent comprises the measurement of the value of at least one physical-chemical parameter such as defined hereinabove by means of the measuring unit 40.

In particular, during this step, the imaging tool 45 is used to form images of the or of each zone of confluence between the sweat coming from the or from each secondary channel 9 and the antiperspirant product flowing in the main channel 7.

According to the nature of the imaging tool 45 used, these images are for example phase contrast microscopy images, such as that shown in FIG. 4, or fluorescence images.

In the case where images are produced fluorescence, a fluorescent product is added such as fluorescein to the sweat injected into the secondary channels 9.

Alternatively or as an option, the pressure is continuously measured in the or each secondary channel 9 by means of the pressure sensor or sensors 42.

Finally, during the step of evaluating the efficacy of the antiperspirant product, the value of the or of each physical-chemical parameter determined in the preceding step is compared with the predefined threshold value, for example by means of the interpretation unit 48.

These values can in particular be Boolean values. For example, the physical-chemical parameter measured is the formation or not of a clog, and it is concluded that the antiperspirant product tested is effective if the formation of a clog is observed during the method. If no formation of a clog is observed, non-efficacy is concluded for the antiperspirant product.

The method of evaluation according to the invention was implemented with the following antiperspirant agents: alun (aluminum sulfate and potassium), ACH and the Aluminum Zirconium Glycine (AZG) complex.

These tests were conducted with the microfluidic chip 4 described hereinabove, and by using as imaging tool 45 a phase contrast microscope.

The injection of the sweat and of the antiperspirant product was carried out according to the sequence described in the table 1.

The results of these tests are summarized in the table 2 hereinbelow.

TABLE 2

| Antiperspirant product | Concentration | Evaluation result |
|---|---|---|
| Alun | 10% | Non-effective |
| AZG | 15% | Effective |
| ACH | 5% | Effective |
| ACH | 15% | Effective |

It is considered that the antiperspirant product is effective when, by means of the imaging tool, the formation of a clog 64 is observed in the secondary channel 9 at the confluence between the secondary channel 9 and the main channel 7, as shown in FIG. 4, with this clog 64 preventing the flow of the sweat contained in the secondary channel 9 in the main channel 7.

It is considered that the antiperspirant product is not effective when no clog is formed in the secondary channel 9. In this case, the sweat of the secondary channel 9 can freely flow in the main channel 7.

These tests conducted by means of the evaluation system according to the invention demonstrate the evaluation efficacy of this system. Indeed, ACH and AZG are known to be effective antiperspirant agents in vivo, while alun is known to be an antiperspirant agent that is not effective in vivo. However, the system according to the invention produces the expected results for these known antiperspirant agents. It therefore gives low evaluation results.

The method of evaluation of the efficacy of an antiperspirant product according to the invention is particularly advantageous.

Indeed, thanks to the use of the microfluidic chip 5, of which the secondary channels 9 reproduce the confinement that exists on the sweat channels and for which the network of secondary channels 9 and main channels 7 reproduce the distribution capacity of the antiperspirant product in the sweat, the method according to the invention gives results that are reliable and close to those that would be obtained using in vivo tests.

Moreover, it is relatively inexpensive to implement, in particular since it does not involve expensive in vivo tests.

Finally, it is also rapid to implement, and therefore makes it possible to rapidly test a large number of antiperspirant products.

The duration of the implementation of the method is particularly low when the injection flow rates, in particular for the sweat, are variable over time. Indeed, the variation in the flow rate according to the steps of filling, of distributing and/or of filling makes it possible to conduct each experiment in a much shorter time than if the sweat were maintained constant.

For example, the predefined variation of the flow rate of sweat during successive steps (filling, distributing and unclogging) such as is defined in table 1 make it possible to conduct each experiment in less than 45 minutes, while several hours would be required if the flow rate of sweat is maintained constant and equal to 0.1 nL/s.

According to an alternative of the evaluation system 1, the microfluidic chip 5 does not comprise inlet channels 17. The main channel 7 opens onto the surface of the microfluidic chip 5 in such a way as to be able to be connected directly to the second injection device 52. The antiperspirant agent inlet 13 of the main channel 7 is flush with the surface of the microfluidic chip 5.

Figure 6:
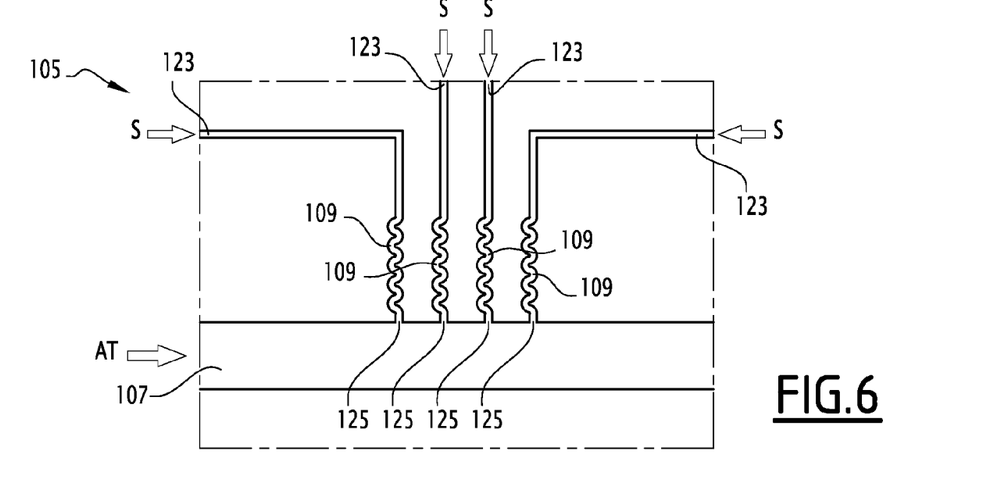
FIG. 6 is a diagrammatical top view of a portion of the evaluation system of FIG. 5.

An evaluation system 101 according to a second embodiment is represented in FIGS. 5 and 6.

This evaluation system 101 differs from the evaluation system 1 according to the first embodiment only by the characteristics described in what follows.

In particular, the evaluation system 101 comprises a microfluidic chip 105 similar to the microfluidic chip 5 of the evaluation system 1. The microfluidic chip 105 differs from the microfluidic chip 5 in that it does not comprise distribution channels. It therefore does not comprise a set 27 of secondary channels 9 such as those defined in reference to the first embodiment.

The microfluidic chip 105 comprises secondary channels 109 that differ from the secondary channels 9 only in that they are independent between them from a fluidic standpoint. As such, each secondary channel 109 is able to be connected directly as an inlet to the first injection device 50. Each secondary channel 109 opens onto the outside of the microfluidic chip 105.

Each secondary channel 109 comprises a sweat inlet 123 flush with the surface of the microfluidic chip 105, through which the sweat enters into the secondary channel 109, and a sweat outlet 125 through which the secondary channel 109 opens into the main channel 107.

All of the secondary channels 109 are able to be supplied with sweat independently from the sweat source 3.

The use of independent secondary channels 109 avoids the pressure imbalances that can occur between the secondary channels 9 of the same set 27 of secondary channels 9 of the microfluidic chip 5 according to the first embodiment.

In this embodiment, certain secondary channels 109 are for example curved, in particular at a right angle.

The secondary channels 109 sinuous in shape are not necessarily sinuous over their entire length. They have a sinuous shape at least in their downstream section comprising the sweat outlet 125. They can comprise a straight section upstream of this downstream section sinuous in shape. The downstream section sinuous in shape advantageously has a length at least between 1 mm and 5 mm.

Optionally, the microfluidic chip 105 further differs from the microfluidic chip 5 described in reference to FIGS. 1 and 2 in that it comprises at least two networks of channels each comprising a main channel 107 and at least two secondary channels 109 opening into this main channel 107. Such a network is shown in more detail in FIG. 6.

The main channels 107 are similar to the main channel 7 described hereinabove. They each comprise an antiperspirant agent inlet 113 and an antiperspirant agent outlet 115.

The relations between the main channel 7 and the secondary channels 9 of the same network are similar to those described in reference to the first embodiment.

For example, the microfluidic chip 5 comprises four networks of channels each comprising a main channel 107 and four secondary channels 109 opening into the main channel 107.

For example, all of the secondary channels 109 opening into the same main channel 107 have the same shape and/or the same diameter.

When the microfluidic chip 105 comprises several networks of channels, the secondary channels 109 of the various networks of channels have for example characteristics of shape and/or of dimensions that are different.

The number of secondary channels 109 is for example identical to all of the networks of channels of the same microfluidic chip 105.

Alternatively, at least two networks of channels have a different number of secondary channels 109.

Preferably, all of the main channels 107 of the same microfluidic chip 105 have the same diameter.

In the embodiment shown in FIGS. 5 and 6, the microfluidic chip 105 does not comprise inlet channels. The or each main channel 107 opens onto the surface of the microfluidic chip 105 in such a way that it can be connected directly to the second injection device 52. The antiperspirant agent inlet 113 of the or of each main channel 107 is flush with the surface of the microfluidic chip 5.

The method of manufacture of the evaluation system 101 according to the second embodiment is similar to the method according to the first embodiment.

The method of evaluation of the efficacy of an antiperspirant product by means of the evaluation system 101 according to the second embodiment is substantially identical to that according to the first embodiment.

Figure 7:
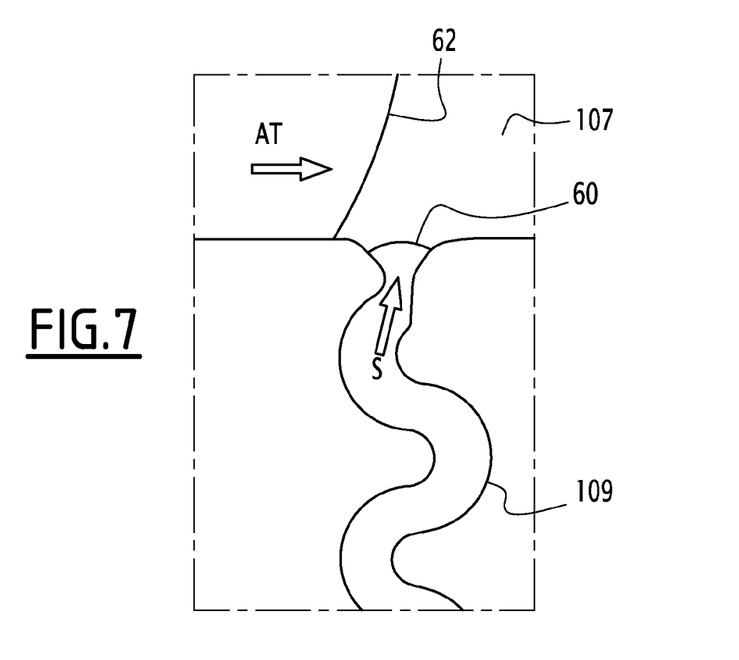
FIG. 7 is a diagrammatical top view of a portion of the evaluation system of FIG. 5 taken during the filling of the channels of the microfluidic chip.

Advantageously, during this step of filling, the sweat is injected into one of the secondary channels 109, and the injecting of sweat into this secondary channel 109 is stopped when the sweat arrives at the confluence of the main channel 107. More particularly, the injecting of sweat is stopped when the meniscus 60 of the sweat arrives at the confluence of the main channel 107. Then, the antiperspirant product is injected into the main channel 107, and the injecting of antiperspirant product into the main channel 107 is stopped when the meniscus 62 of the antiperspirant product arrives in the vicinity of the inlet of the secondary channel 109 wherein the sweat was injected in the preceding step.

FIG. 7 shows the position of the meniscus 60 of the sweat in the secondary channel 109 when the injecting of sweat is stopped and the position of the meniscus 62 of the antiperspirant product when the injection of antiperspirant product is stopped, i.e. when it is in the vicinity of the inlet of the secondary channel 109.

The injection of sweat into the secondary channel 109 considered and the injection of antiperspirant product into the main channel 107 are then started again in such a way as to allow the contact between the sweat of the secondary channel 109 considered and the antiperspirant product.

This injection sequence makes it possible to prevent the rising back of the antiperspirant product into the secondary channel 109 during the filling.

When the microfluidic chip 104 comprises more than one secondary channel 109, this filling process is repeated successively for each secondary channel 109 that is desired to be used by following the direction of flow of the antiperspirant product.

The evaluation system 101 and the evaluation method using this evaluation system 101 has the same advantages as those described hereinabove. They have moreover increased reliability thanks to the independence of the secondary channels 109.

The invention claimed is:

1. A microfluidic evaluation system for evaluating in vitro the efficacy of an antiperspirant product, comprising:
 a natural or artificial sweat source; and
 a microfluidic chip comprising:
  a main flow channel for the antiperspirant product; and
  at least one secondary flow channel for the sweat, the or each secondary channel comprising a sweat inlet that can receive sweat from the sweat source and a sweat outlet through which the secondary channel opens into the main channel, the or each secondary channel having a diameter of less than 100 µm and
  wherein the sweat source is connected to the or each secondary channel via a sweat injection device, disposed outside of the microfluidic chip and configured to inject the sweat at a controlled rate.

2. The system according to claim 1, wherein the or at least one of the secondary channels is straight.

3. The system according to claim 1, wherein the or at least one of the secondary channels comprises at least one section sinuous in shape.

4. The system according to claim 1, further comprising a measuring unit able to determine at least one physical-chemical parameter that represents the efficacy of the antiperspirant product flowing in the main channel.

5. The system according to claim 4, wherein the measuring unit comprises at least a pressure sensor able to measure the pressure in the or each secondary channel.

6. The system according to claim 4, wherein the measuring unit comprises an imaging tool able to form an image of the zone of confluence between the sweat coming from the or from each secondary channel and the antiperspirant product flowing in the main channel.

7. The system according to claim 1, further comprising:
a first injection device connected to the sweat source and configured to inject the sweat from the sweat source into the or each secondary channel at a determined injection flow rate;
a second injection device configured to inject the antiperspirant product into the main channel at a determined injection flow rate.

8. The system according to claim 1, wherein the main channel is open over its entire length over a portion of its circumference.

9. The system according to claim 1, wherein the microfluidic chip comprises at least:
a set of secondary channels comprising at least two secondary channels, and
at least one channel for distributing sweat comprising a sweat distribution inlet intended to be connected to the sweat source and sweat distribution outlets through which the distribution channel opens into the secondary channels of the set in such a way that the secondary channels of the set of secondary channels are supplied with sweat in parallel by the channel for distributing sweat.

10. The system according to claim 9, wherein at least one set of secondary channels substantially has a comb shape, the secondary channels forming the teeth of the comb, the or each set of secondary channels opening into the same main channel.

11. The system according to claim 1, wherein the walls of the or of each secondary channel are functionalized by proteins.

12. The system according to claim 1, wherein the main channel has a cross-section that is strictly greater than the cross-section of the or of each secondary channel.

13. A method for evaluating the efficacy of an antiperspirant product, comprising the steps of:
supplying a microfluidic evaluation system according to claim 1;
injecting sweat into the or each secondary channel of the microfluidic chip from the sweat source;
injecting antiperspirant product into the main channel;
determining at least one physical-chemical parameter that represents the efficacy of the antiperspirant product; and
evaluating the efficacy of the antiperspirant product using the or each physical-chemical parameter measured.

14. The method according to claim 13, wherein the sweat is injected into the or each secondary channel in pulse mode or in continuous mode.

15. The method according to claim 14 wherein the step of injecting sweat comprises:
injecting sweat into the or each secondary channel at a filling flow rate until the or each secondary channel is filled with sweat, then
injecting sweat into the or each secondary channel at a distribution flow rate strictly less than the filling flow rate.

16. The method according to claim 15, wherein the step of injecting sweat comprises:
injecting sweat into the or each secondary channel at a distribution flow rate; then
injecting sweat into the or each secondary channel at an unclogging flow rate that is strictly greater than the distribution flow rate, and advantageously progressively increasing over time.

17. A microfluidic chip comprising:
a main flow channel suited for the flow of antiperspirant product; and
at least one secondary channel suited for the flow of sweat, the or each secondary channel comprising a sweat inlet able to receive the sweat coming from a natural or artificial sweat source and a sweat outlet through which the secondary channel opens into the main channel, the or each secondary channel having a diameter of less than 100 μm; and
a sweat injection device, external to the microfluidic device, and configured to inject sweat into the sweat inlet at a controlled rate.

18. The microfluidic according to claim 17, comprising at least:
a set of secondary channels comprising at least two secondary channels, and
at least one channel for distributing sweat comprising a sweat distribution inlet intended to be connected to the sweat source and sweat distribution outlets through which the distribution channel opens into the secondary channels of the set in such a way that the secondary channels of the set of secondary channels are supplied with sweat in parallel by the channel for distributing sweat;
at least one set of secondary channels substantially has a comb shape, the secondary channels forming the teeth of the comb,
the or each set of secondary channels opening into the same main channel.

19. The system according to claim 2, wherein the or at least one of the secondary channels comprises at least one section sinuous in shape.

20. The system according to claim 2, further comprising a measuring unit able to determine at least one physical-chemical parameter that represents the efficacy of the antiperspirant product flowing in the main channel.

21. The system according to claim 1, wherein the sweat source comprises a container containing natural sweat, artificial sweat or a mixture of natural and artificial sweat.

22. A microfluidic evaluation system for evaluating in vitro the efficacy of an antiperspirant product, comprising:
a natural or artificial sweat source; and
a microfluidic chip comprising:
a main flow channel for the antiperspirant product; and
at least one secondary flow channel for the sweat, the or each secondary channel comprising a sweat inlet configured to receive sweat from the sweat source and a sweat outlet through which the secondary channel opens into the main channel, the or each secondary channel having a diameter of less than 100 µm and wherein the microfluidic chip comprises at least:
- a set of secondary channels comprising at least two secondary channels, and
- at least one channel configured for distributing sweat comprising a sweat distribution inlet connected to the sweat source and sweat distribution outlets through which the distribution channel opens into the secondary channels of the set in such a way that the secondary channels of the set of secondary channels are supplied with sweat in parallel by the channel for distributing sweat.

23. A microfluidic evaluation system for evaluating in vitro the efficacy of an antiperspirant product, comprising:
a natural or artificial sweat source; and
a microfluidic chip comprising:
  a main flow channel for the antiperspirant product; and
  at least one secondary flow channel for the sweat, the or each secondary channel comprising a sweat inlet configured to receive sweat from the sweat source and a sweat outlet through which the secondary channel opens into the main channel, the or each secondary channel having a diameter of less than 100 µm and wherein the microfluidic chip comprises at least:
  a set of secondary channels comprising at least two secondary channels, and
at least one channel configured for distributing sweat comprising a sweat distribution inlet be connected to the sweat source and sweat distribution outlets through which the distribution channel opens into the secondary channels of the set in such a way that the secondary channels of the set of secondary channels are supplied with sweat in parallel by the channel for distributing sweat and
wherein at least one set of secondary channels substantially has a comb shape, the secondary channels forming the teeth of the comb, the or each set of secondary channels opening into the same main channel.

* * * * *